(12) United States Patent
O'Heeron

(10) Patent No.: US 7,320,694 B2
(45) Date of Patent: Jan. 22, 2008

(54) OBTURATOR TIP

(75) Inventor: Peter T. O'Heeron, Houston, TX (US)

(73) Assignee: CooperSurgical, Inc., Trumbull, CT (US)

( * ) Notice: Subject to any disclaimer, the term of this patent is extended or adjusted under 35 U.S.C. 154(b) by 695 days.

(21) Appl. No.: 10/799,750

(22) Filed: Mar. 11, 2004

(65) Prior Publication Data

US 2005/0203559 A1   Sep. 15, 2005

(51) Int. Cl.
*A61B 17/32* (2006.01)

(52) U.S. Cl. .................... 606/167; 606/185

(58) Field of Classification Search ........ 606/167, 606/185
See application file for complete search history.

(56) References Cited

U.S. PATENT DOCUMENTS

| | | | |
|---|---|---|---|
| 5,342,315 A | 8/1994 | Rowe et al. | |
| 5,350,364 A | 9/1994 | Stephens et al. | |
| 5,350,393 A | 9/1994 | Yoon | |
| 5,385,553 A | 1/1995 | Hart et al. | |
| 5,405,328 A | 4/1995 | Vidal et al. | |
| 5,407,433 A | 4/1995 | Loomas | |
| 5,411,515 A | 5/1995 | Harber et al. | |
| 5,431,635 A | 7/1995 | Yoon | |
| 5,512,053 A | 4/1996 | Pearson et al. | |
| 5,522,833 A * | 6/1996 | Stephens et al. | 606/185 |
| 5,538,509 A | 7/1996 | Dunlap et al. | |
| 5,549,564 A | 8/1996 | Yoon | |
| 5,551,947 A | 9/1996 | Kaali | |
| 5,554,137 A | 9/1996 | Young et al. | |
| 5,554,167 A | 9/1996 | Young et al. | |
| 5,569,289 A | 10/1996 | Yoon | |
| 5,584,850 A | 12/1996 | Hart et al. | |
| 5,591,190 A | 1/1997 | Yoon | |
| 5,607,440 A | 3/1997 | Danks et al. | |
| 5,609,604 A | 3/1997 | Schwemberger et al. | |
| 5,628,732 A | 5/1997 | Antoon, Jr. et al. | |
| 5,645,076 A | 7/1997 | Yoon | |
| 5,645,556 A | 7/1997 | Yoon | |
| 5,669,885 A | 9/1997 | Smith | |
| 5,674,184 A | 10/1997 | Hassler, Jr. | |
| 5,674,237 A | 10/1997 | Ott | |
| 5,685,820 A | 11/1997 | Riek et al. | |

(Continued)

OTHER PUBLICATIONS

Core Dynamics, Inc. "Disposable Trocar and Resuable Automatic Valve Cannula System" Entree 1991.

(Continued)

*Primary Examiner*—Michael J. Hayes
*Assistant Examiner*—Michael G. Mendoza
(74) *Attorney, Agent, or Firm*—Clarence E. Eriksen & Associates, P.C.

(57) ABSTRACT

The present invention provides an obturator tip having a rigid, elongated, distal section having a blunt, rounded, distal end designed to separate tissue. The distal section is connected to a proximal section by a central section having tapered outer surfaces. The obturator tip of the present invention is equipped with arc shaped blades positioned on opposite sides of the tip and 180 degrees apart from each other. In one embodiment, the arc shaped blades are positioned rearwardly with respect to the distal section of the obturator. This feature of the present invention allows the elongated distal section to create a small, non-cutting tissue separating track prior to blade contact with the patient.

3 Claims, 4 Drawing Sheets

U.S. PATENT DOCUMENTS

| | | |
|---|---|---|
| 5,697,947 A | 12/1997 | Wolf et al. |
| 5,720,761 A | 2/1998 | Kaali |
| 5,752,938 A | 5/1998 | Flatland et al. |
| 5,792,113 A | 8/1998 | Kramer et al. |
| 5,797,944 A | 8/1998 | Nobles et al. |
| 5,810,863 A | 9/1998 | Wolf et al. |
| 5,817,061 A * | 10/1998 | Goodwin et al. ...... 604/164.03 |
| 5,827,228 A | 10/1998 | Rowe |
| 5,989,224 A | 11/1999 | Exline et al. |
| 6,099,544 A | 8/2000 | Wolf et al. |
| 6,238,407 B1 | 5/2001 | Wolf et al. |
| 6,280,417 B1 | 8/2001 | Bohannon et al. |
| 6,340,358 B1 | 1/2002 | Bohannon et al. |
| 6,544,277 B1 | 4/2003 | O'Heeron |
| 6,551,282 B1 | 4/2003 | Exline et al. |
| 6,656,198 B2 * | 12/2003 | Tsonton et al. ............. 606/167 |
| 6,783,516 B2 | 8/2004 | O'Heeron |

OTHER PUBLICATIONS

Marlow Surgical Technologies, Inc. Hasson SAC TM Stable Access Cannula TM offers maximum stability for advanced laparoscopic procedures.

* cited by examiner

OBTURATOR TIP

FIELD OF THE INVENTION

The present invention relates generally to surgical instruments and, more particularly, to an obturator for use in conjunction with one or more trocars for penetrating an anatomical cavity of a patient to provide communication with the cavity during a surgical procedure.

BACKGROUND OF THE INVENTION

Endoscopic surgery is a significant method of performing surgical operations and has become the surgical procedure of choice due to its patient care advantages over "open surgery." A particular type of endoscopic surgery is laparoscopic surgery. A significant advantage of laparoscopic surgery over open surgery is the decreased post-operative recovery time. In most instances, a patient is able to leave the hospital within hours after laparoscopic surgery has been performed, whereas with open surgery, a patient requires several days of hospital care to recover. Additionally, laparoscopic surgery achieves decreased incidents of post-operative abdominal adhesions, decreased post-operative pain, and enhanced cosmetic results.

Conventionally, a laparoscopic surgical procedure begins with the insufflation of the abdominal cavity with carbon dioxide. The introduction of this gas into the abdominal cavity lifts the abdominal wall away from the internal viscera. The abdominal wall is then pierced or penetrated with a device known as a trocar. A trocar includes a housing assembly, a cannula assembly attached to the housing assembly to form a bore through the trocar, and a piercing element called an obturator. The obturator slides through an access port formed on the upper end of the housing assembly and through the bore of the trocar. After insertion of the trocar through the abdominal wall of the patient, the obturator is removed by the surgeon while leaving the cannula protruding through the abdominal wall. The cannula may be fixed in place by using a fascia device, and laparoscopic instruments can then be inserted through the cannula to view internal organs and to perform surgical procedures.

Traditionally, the piercing tip of the obturator of a trocar has employed a sharp cutting blade to assist the surgeon in penetrating the abdominal wall. These obturators with cutting tips cut the tissue and muscle of the patient when inserted into the patient, and recovery time from the trauma of this cutting of tissue and muscle is necessary. Moreover, since the cutting tips are sharp, costly safety shield mechanisms are employed in trocars which operate to cover the obturator tip a short time after the obturator passes through the abdominal wall of the patient.

Unfortunately, such devices are not always effective. First, the external shield tends to provide an additional impediment to insertion, thus requiring greater incision force and compounding the risk of follow through injury. Second, the force of the safety shield passing through the skin tissue often results in tearing and other damage at the incision point. In addition to needlessly increasing the size of a surgical wound, this also tends to compromise the foundation of the cannula and may lead to undesirable leaks of fluids and gases during the operation. Third, many physicians complain that the recoil from the safety shield at almost the same moment as the trocar insertion tends to disorient them as to the precise location of the trocar after insertion. This results in wasted time and effort to reorient the trocar and greater risk of internal damage during the period of reorientation.

There remains a need for an obturator capable of piercing and separating tissue so as to lessen the risk of follow through injury.

SUMMARY OF THE INVENTION

Accordingly, the present invention provides an obturator capable of operation with a shieldless trocar. The obturator of the present invention is equipped with an obturator tip designed to pierce and separate tissue in preparation for laparoscopic surgery. In one embodiment, the obturator tip of the present invention provides a rigid, elongated, distal section having a blunt, rounded, distal end designed to separate tissue. The distal section is connected to a proximal section by a central section having tapered outer surfaces. In one embodiment, the diameter of the proximal section is greater than the diameter of the distal section. This feature of the present invention allows for increasing diameter from the distal section to the proximal section in order to allow gradual separation of tissue.

The obturator tip of the present invention is equipped with arc shaped blades positioned on opposing sides of the tip. In one embodiment, the arc shaped blades may be positioned rearwardly with respect to the distal section of the obturator. This feature of the present invention allows the elongated distal section to create a small, non-cutting, tissue separating track prior to blade contact with the patient.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing; it being understood that the drawings contained herein are not necessarily drawn to scale; wherein.

DETAILED DESCRIPTION OF THE INVENTION

Figure 1:
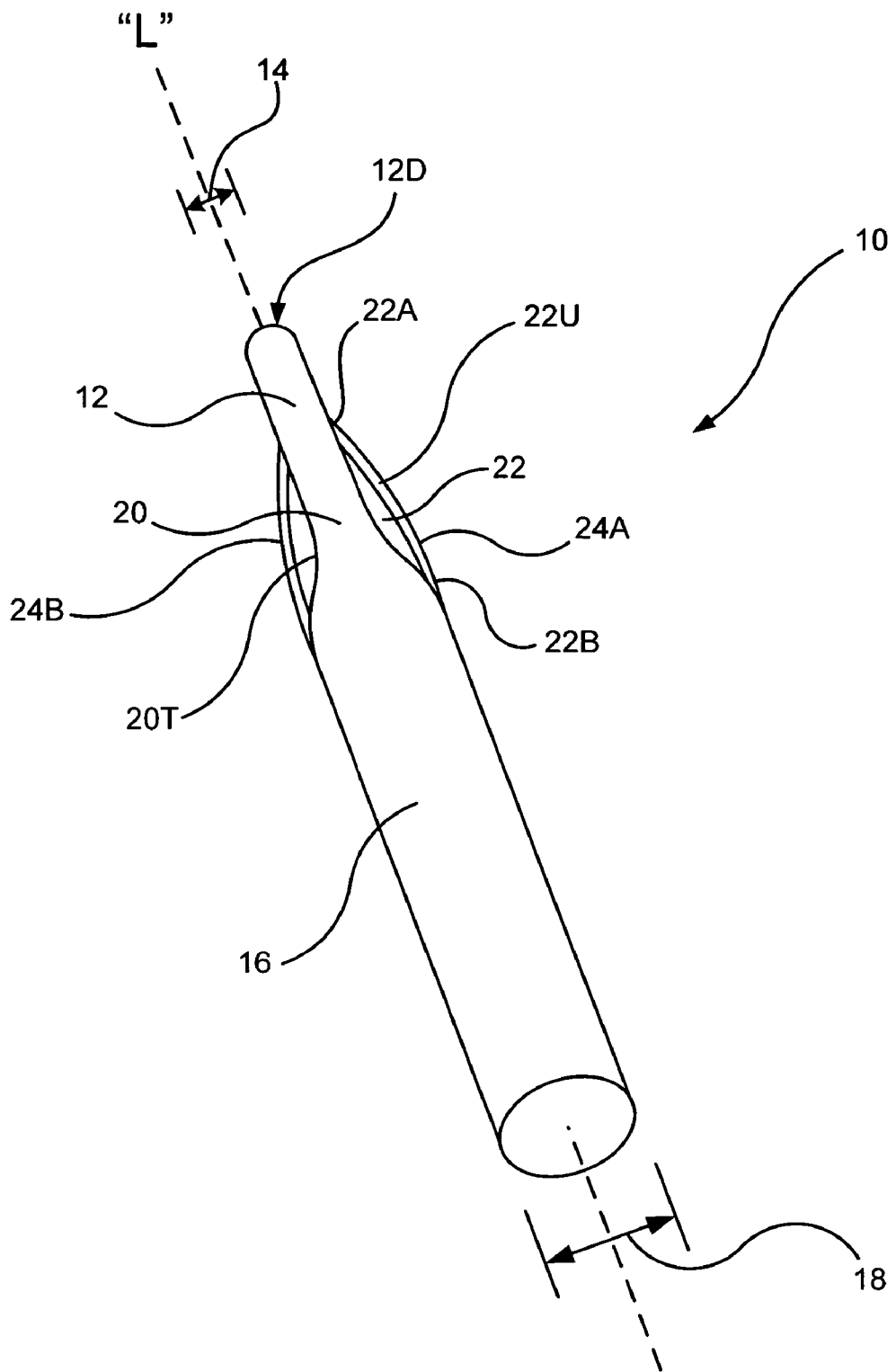
FIG. 1 is a perspective view of the obturator tip of one embodiment of the present invention.
Figure 2:
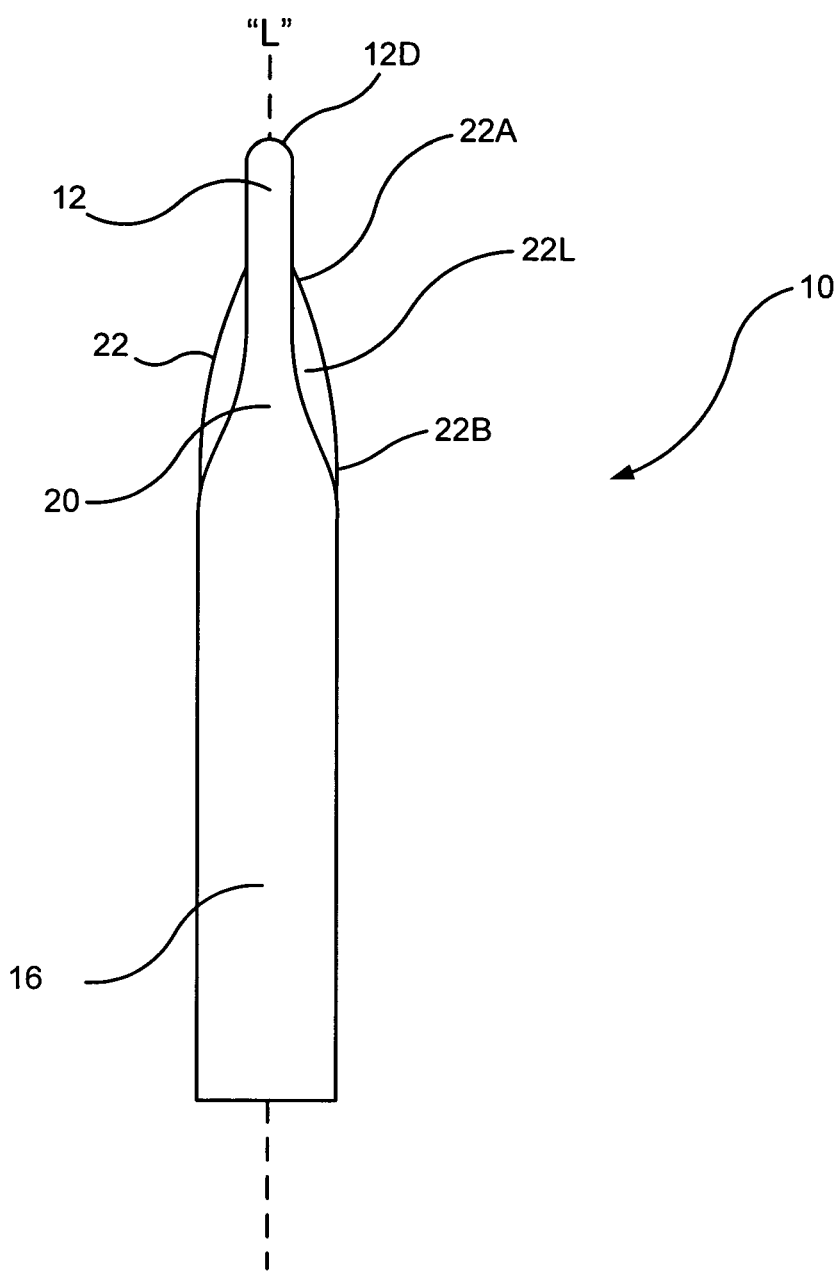
FIG. 2 is a bottom, elevation view of the obturator tip of one embodiment of the present invention.
Figure 3:
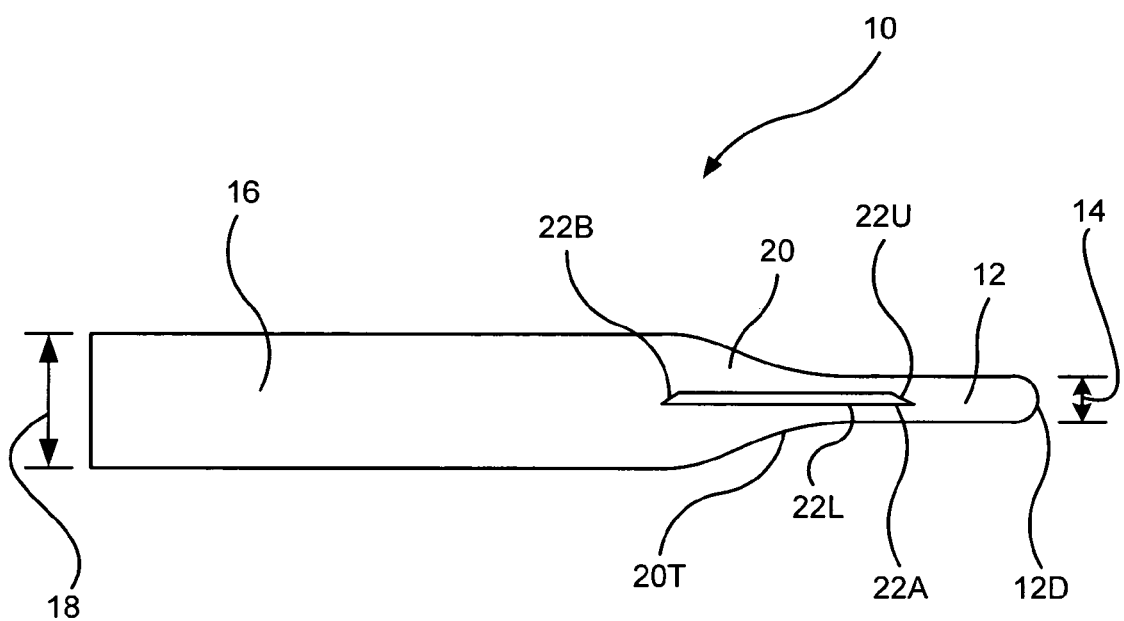
FIG. 3 is a right side elevation view of the obturator tip of one embodiment of the present invention.
Figure 4:
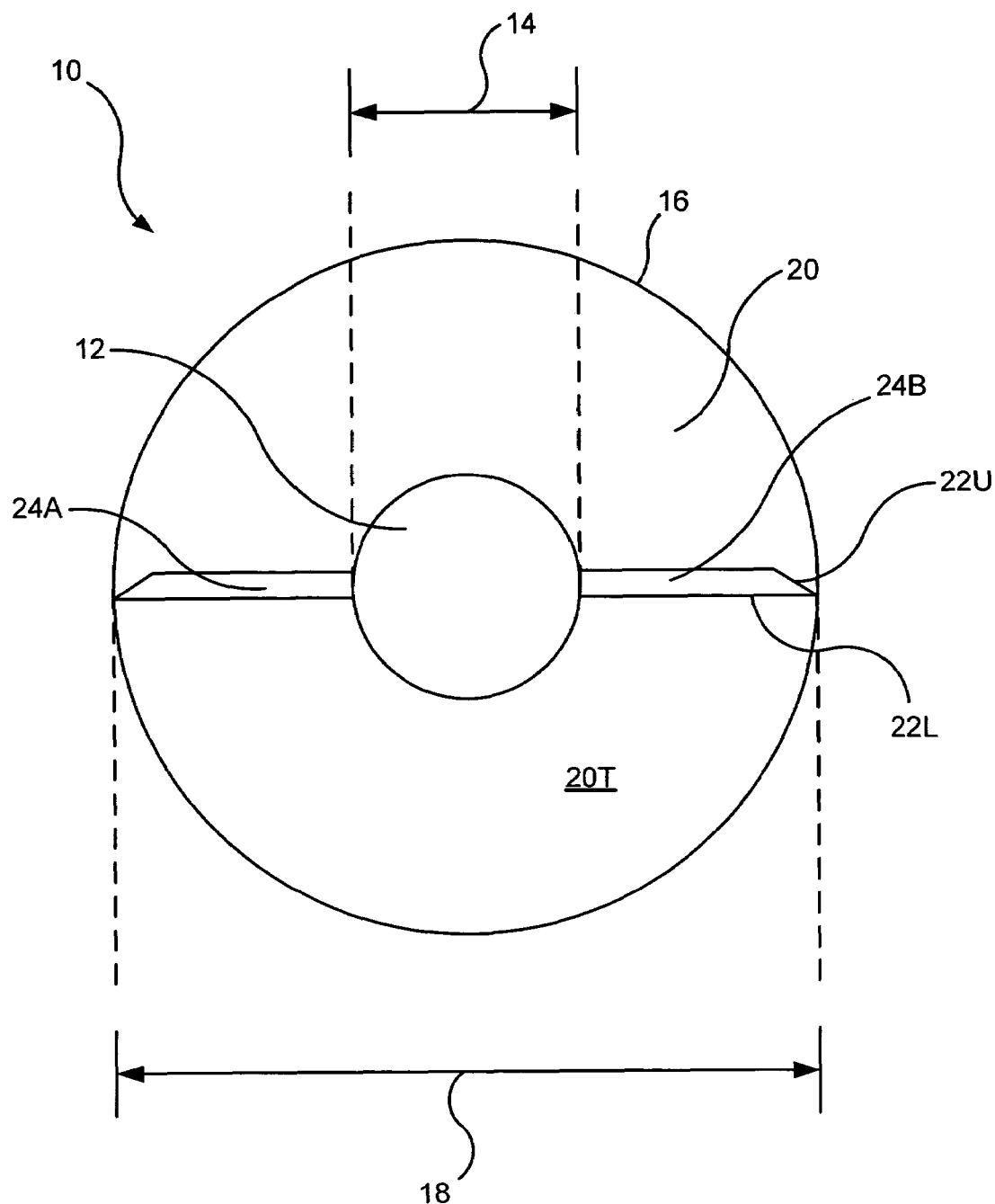
FIG. 4 is a front, elevation view of the obturator tip of one embodiment of the present invention.

The present invention is herein described as a substantially rigid obturator tip (10) for use in conjunction with one or more trocars for penetrating an anatomical cavity of a patient. Referring to the Figures, the obturator tip of the present invention provides a distal section (12) having a distal end (12D) designed to separate tissue. In one embodiment, the distal end (12D) of the distal section (12) is blunt and rounded to insure that no sharp cutting surfaces are presented upon initial insertion of the obturator tip into the patient.

The obturator tip (10) of the present invention provides a central section (20) for connecting the distal section (12) to a substantially cylindrical proximal section (16). In one embodiment, the central section (20) is equipped with smooth, tapered, outer surfaces (20T) designed to vary the diameter of the central section relative to the longitudinal axis (L) of the obturator tip (10). In one embodiment, the outer surfaces (20T) of the central section (20) are tapered to provide increasing diameter as taken from the distal section (12) to the proximal section (16). This feature of the present invention allows the obturator tip (10) to gradually widen the degree to which tissue is separated upon continued insertion of the obturator into the body of the patient. It being understood that the outer surfaces of the central section may be tapered in a linear or non-linear fashion, depending on surgical requirements.

In one embodiment, the distal section (12) of the obturator tip of the present invention is elongated and has a substantially uniform diameter (14). The uniform diameter of the distal section allows for continued insertion of the distal section, if desired, without further widening the tissue being separated. In one embodiment, the diameter (18) of the proximal section (16) is greater than the diameter (14) of the distal section (12). This feature of the present invention allows the proximal section to engage the axial bore of the trocar while the distal section gently creates an insertion track of lesser diameter. In one embodiment, both the distal section (12) and the proximal section (16) have uniform diameters and have a generally cylindrical configuration.

The obturator tip (10) of the present invention provides cutting functionality, when appropriate. In one embodiment, a pair of arc shaped blades (22) are attached to, and positioned upon, opposing sides of the obturator tip of the present invention about 180 degrees apart from each other. Such blades (22) are designed to cut and/or separate tissue subsequent to initial, non-cutting separation by the distal section (12) of the obturator tip. The blades (22) of the present invention have upper and lower surfaces (22U and 22L, respectively) and may be tapered as desired, depending upon the surgical application being performed. In one embodiment, the upper surfaces (22U) of the blades (22) taper in a downward direction.

In one embodiment, the upper surface (22U) of each blade converges with the lower surface (22L) at a point at or below the longitudinal axis (L) of the obturator tip (10). Such convergence resulting in a cutting and/or separating edge for engaging tissue. The blades of the present invention have first and second ends (22A and 22B, respectively). The first end (22A) of each blade may be attached to either the distal or central sections (12 and 20, respectively) of the obturator tip while the second end may be attached to the proximal section (16). In one embodiment, the first end of each blade is attached to the distal section of the obturator tip just prior to expansion of the diameter of the central section (20).

In another embodiment, a generally oval shaped insert for molded blade (22) residing partially within the obturator tip is provided in lieu of the aforementioned pair of blades. In this embodiment, the insert blade is equipped with two arc shaped wing elements (24A and 24B) located on opposing sides of the insert blade about 180 degrees apart from each other. The wing elements of the present invention protrude outwardly away from the longitudinal axis (L) of the obturator tip and also have upper and lower surfaces (22U and 22L, respectively), as described above. In one embodiment, the upper surface of each wing element tapers in a downward direction.

The obturator tip of the present invention has a number of advantages over known obturators. First, it may be used on the initial penetration of the patient when the location of a vital obstruction may not be known. Second, the obturator tip of the present invention does not require a shielding mechanism. Thus, the obturator is lighter, less expensive, and does not require assembly prior to shipment.

The unique design of the obturator tip of the present invention creates a smaller wound than a cutting blade, which results in quicker healing and better fascia fixation of the cannula. Finally, use of an obturator tip in accordance with the present invention results in dilation of the wound track instead of cutting of the wound track, which reduces the risk of herniation.

Although the invention has been described with reference to specific embodiments, this description is not meant to be construed in a limited sense. Various modifications of the disclosed embodiments, as well as alternative embodiments of the invention, will become apparent to persons skilled in the art upon reference to the description of the invention. It is, therefore, contemplated that the appended claims will cover such modifications that fall within the scope of the invention.

I claim:

1. An obturator tip having a longitudinal axis, said tip comprising:
   an elongated distal section having a first diameter, said distal section having a blunt, rounded, distal end for separating tissue;
   an elongated proximal section having a second diameter;
   a central section for connecting said distal section and said proximal section; and
   a pair of blades located on opposing sides of said tip, said blades positioned about 180 degrees apart from each other, wherein a first end of at least one of said blades is attached to said distal section of said obturator tip and wherein a second end of at least one of said blades is attached to said proximal section of said obturator tip.

2. An obturator tip having a longitudinal axis, said tip comprising:
   an elongated distal section having a first diameter, said distal section having a blunt, rounded, distal end for separating tissue;
   an elongated proximal section having a second diameter;
   a central section for connecting said distal section and said proximal section; and
   a pair of blades located on opposing sides of said tip, said blades positioned about 180 degrees apart from each other, wherein said central section further comprises tapered outer surfaces for connecting said proximal section and said distal section and wherein said outer surfaces of said central section taper in a non-linear fashion.

3. An obturator tip having a longitudinal axis, said tip comprising:
   an elongated distal section having a first diameter, said distal section having a blunt, rounded, distal end for separating tissue;
   a proximal section having a second diameter;
   a central section for connecting said distal section and said proximal section; and
   an insert or molded blade residing partially within said tip, said blade having two wing elements located on opposing sides of said blade and protruding outwardly away from said longitudinal axis, wherein said central section comprises tapered outer surfaces for connecting said proximal section and said distal section and wherein said outer surfaces of said central section taper in a non-linear fashion.

* * * * *